US010034854B2

(12) United States Patent
Lomuscio et al.

(10) Patent No.: US 10,034,854 B2
(45) Date of Patent: *Jul. 31, 2018

(54) PHARMACEUTICAL COMPOSITION WITH IMPROVED BIOAVAILABILITY

(71) Applicant: Hoffmann-La Roche Inc., Nutley, NJ (US)

(72) Inventors: Steve Lomuscio, Union, NJ (US); Hua Ma, Wayne, NJ (US); Michael Allen Matchett, Montville, NJ (US); Harpreet K. Sandhu, West Orange, NJ (US); Navnit Hargovindas Shah, Clifton, NJ (US); Yu-E Zhang, Wayne, NJ (US)

(73) Assignee: HOFFMAN-LA ROCHE INC., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/200,419

(22) Filed: Jul. 1, 2016

(65) Prior Publication Data

US 2017/0000764 A1 Jan. 5, 2017

Related U.S. Application Data

(62) Division of application No. 14/159,679, filed on Jan. 21, 2014, now Pat. No. 9,427,427.

(60) Provisional application No. 61/755,074, filed on Jan. 22, 2013.

(51) Int. Cl.
| | |
|---|---|
| *A61K 31/40* | (2006.01) |
| *A61K 9/10* | (2006.01) |
| *A61K 9/14* | (2006.01) |
| *A61K 9/16* | (2006.01) |
| *A61K 9/20* | (2006.01) |
| *A61K 9/28* | (2006.01) |
| *A61K 47/38* | (2006.01) |

(52) U.S. Cl.
CPC .............. *A61K 31/40* (2013.01); *A61K 9/10* (2013.01); *A61K 9/146* (2013.01); *A61K 9/1641* (2013.01); *A61K 9/2027* (2013.01); *A61K 9/2054* (2013.01); *A61K 9/28* (2013.01); *A61K 47/38* (2013.01)

(58) Field of Classification Search
CPC .................................................... A61K 31/40
See application file for complete search history.

(56) References Cited

U.S. PATENT DOCUMENTS

2014/0128431 A1* 5/2014 LaRoche et al. .. A61K 31/4709
514/314

FOREIGN PATENT DOCUMENTS

| CN | 102871950 A | 1/2013 | |
|---|---|---|---|
| WO | WO 2010114928 A2 * | 10/2010 | .......... C07D 471/04 |
| WO | 2011098398 | 8/2011 | |
| WO | WO 2013139687 A1 * | 9/2013 | ............. A61K 31/40 |

OTHER PUBLICATIONS

European Medicines Agency. "Vermurafenib." (c) Dec. 15, 2011. pp. 1-103.*
Drugs.com. "Copovidone." (c) May 16, 2012. Available from: < http://web.archive.org/web/20120516060920/http://www.drugs.com/inactive/copovidone-27.html >.*
PubChem. "Copovidone." © 2016. Available from: < https://pubchem.ncbi.nlm.nih.gov/compound/270885#section=Top >.*
University of Berlin. "List of Abbreviations". (c) 2016. Available from: < http://www.diss.fu-berlin.de/diss/servlets/MCRFileNodeServlet/FUDISS_derivate_000000001718/8_abbreviations.pdf?hosts= >.*
Zak, K., et al. "Mdm2 and MdmX inhibitors for the treatment of cancer: a patent review (2011-present)." Expert Opin. Ther. Patents. (2013), vol. 23(4), pp. 425-448.*
MediLexicon. "Adjuvant." © 2010. Available from: < http://www.medilexicon.com/medicaldictionary.php?t=1338 >.*
"Overview of pharmaceutical excipients used in tablets and capsules." Drug Topics. (c) Oct. 2008. Available from: < http://drugtopics.modernmedicine.com/drug-topics/news/modernmedicine/modern-medicine-news/overview-pharmaceutical-excipients-used-tablets?page=full >.*
Porter, S.C. "Aqueous Polymeric Dispersions for Film Coating of Pharmaceutical Solid-Dosage Forms." (c) 1991.*
The English translation of the Chinese Office Action, dated Nov. 10, 2016, in the related Chinese Application No. 201480005646.7.
The Singapore Search Report, completed on Jun. 30, 2016, in the related Singapore Application No. 11201504499V.
Shah et al., "Improved Human Bioavailability of Vemurafenib, a Practically Insoluble Drug, Using an Amorphous Polymer-Stabilized Solid Dispersion Prepared by a Solvent-Controlled Coprecipitation Process," J Pharm Sci. Mar. 2013;102(3), pp. 967-981.
Ursolic Acid, PubChem, 2005, 4. Chemical and Physical Properties, [online], retrieved from the Internet: https://pubchem.Ncbi.nlm.nih.gov/compound/Ursolic_acid.
The English translation of the Korean Office Action, dated Sep. 22, 2016, in the corresponding Korean application No. 2015-7019822.

* cited by examiner

*Primary Examiner* — Noble E Jarrell
*Assistant Examiner* — John S Kenyon

(57) ABSTRACT

The invention relates to solid dispersions of poorly water soluble compounds, in particular Compound A as disclosed herein, formed by solvent co-precipitation or spray drying, resulting in improved bioavailability, safety and tolerability of said compounds.

7 Claims, 11 Drawing Sheets

PHARMACEUTICAL COMPOSITION WITH IMPROVED BIOAVAILABILITY

CROSS-REFERENCE TO RELATED APPLICATIONS

This application is a Divisional of pending U.S. application Ser. No. 14/159,679, filed Jan. 21, 2014, which in turn claims the benefit of U.S. Provisional Patent Application Ser. No. 61/755,074, filed Jan. 22, 2013, all of which are hereby incorporated by references in their entireties.

FIELD OF THE INVENTION

The present invention relates to a solid amorphous dispersion of a Micro-precipitated Bulk Powder (MBP), or a spray-dried product, comprising the compound 4-{[(2R, 3S,4R,5S)-4-(4-Chloro-2-Fluoro-Phenyl)-3-(3-Chloro-2-Fluoro-Phenyl)-4-Cyano-5-(2,2-Dimethyl-Propyl)-Pyrrolidine-2-Carbonyl]-Amino}-3-Methoxy-Benzoic Acid, (Compound A) to improve the compound's bio-availability, safety and tolerability.

BACKGROUND OF INVENTION

The present invention relates to a pharmaceutical composition comprising a stabilized solid amorphous dispersion, having high drug load, such as 50%-70%, of an extremely low-solubility compound (Compound A) which resulted in significantly enhanced dissolution and bioavailability over the crystalline form of said compound. The compound 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (Compound A), as well as methods for making it, is disclosed in U.S. Pat. No. 8,354,444 and WO2011/098398.

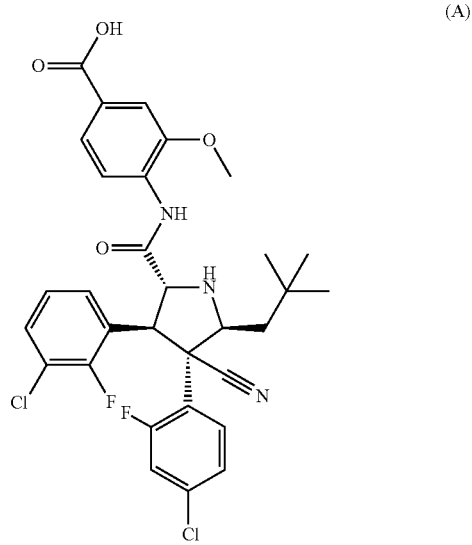 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

(A)

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid ($C_{31}H_{29}Cl_2F_2N_3O_4$) (Compound A) is a potent and selective inhibitor of the p53-MDM2 interaction that activates the p53 pathway and induces cell cycle arrest and/or apoptosis in a variety of tumor types expressing wild-type p53 in vitro and in vivo. Compound A belongs to a novel class of MDM2 inhibitors having potent anti-cancer therapeutic activity, in particular in leukemia such as AML and solid tumors such as for example non-small cell lung, breast and colorectal cancers.

The above-identified international patent application and US Patent describe Compound A in crystalline form and is herein incorporated by reference in its totality. The crystalline form of the compound has an on-set melting point of approximately 277° C. The crystalline forms have relatively low aqueous solubility (<0.05 μg/mL in water) at physiological pHs (which range from pH1.5-8.0) and consequently less than optimal bioavailability (high variability). It is thus desirable to obtain a form of the compound which has improved solubility/dissolution rate and bioavailability.

SUMMARY OF THE INVENTION

The present invention provides an amorphous form of Compound A which is substantially free of crystalline compound. The compound is present in a compound/polymer complex in an amount equal to or greater than 30% of the complex, by weight.

Another aspect of the invention is a pharmaceutical composition comprising the complexes of the invention wherein Compound A is present in a therapeutically effective amount.

Another aspect of the invention is that the complex of the amorphous drug substance with the polymer is stable at high drug load.

Another aspect of the invention is a process for making the complexes of the invention that contains pharmaceutically active compounds in stabilized amorphous form.

The key features of the inventions are:
a) Preparation of stabilized solid amorphous dispersion of Compound A,
b) Drug loading of 10-70% in the final product.
c) While the amorphous solid dispersion is stable at high drug load, such as 70%, the optimal drug loading to achieve the optimal exposure is 10-50%.
d) Use of polymers such as hypromellose acetate succinate, povidone and co-povidone at the level of 30% to 99%,

DETAILED DESCRIPTION OF THE INVENTION

Figure 1:
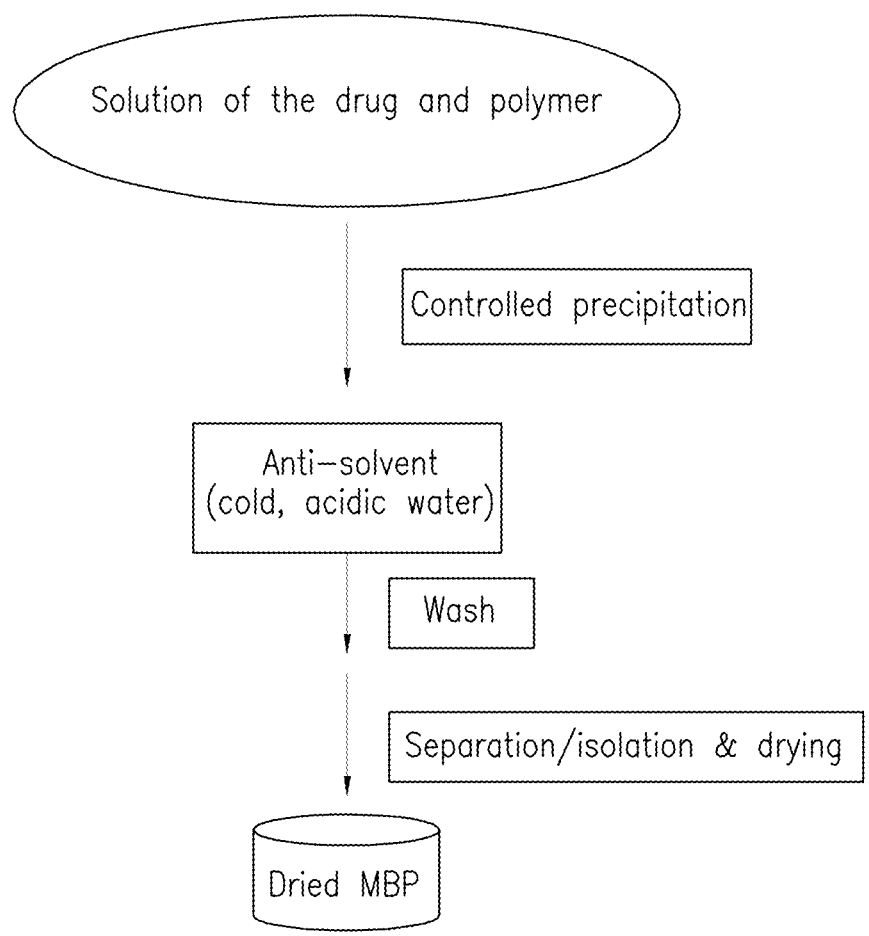
FIG. 1 illustrates the microprecipitation process.
Figure 2:
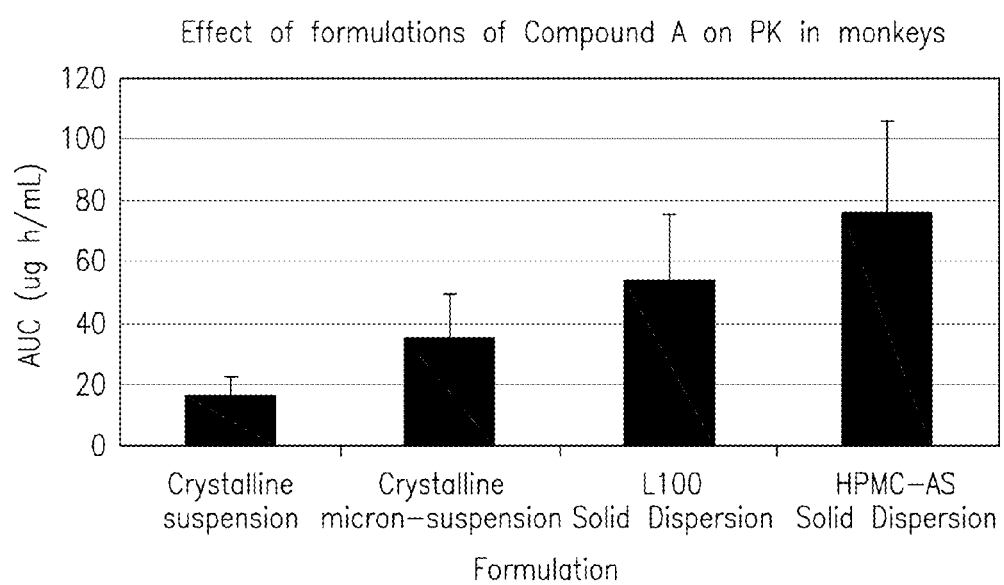
FIG. 2 illustrates the exposure of compound A in monkeys from different formulation strategies: crystalline (as-is) suspension, crystalline micron suspension, solid dispersion with EUDRAGIT L100® (Poly(methacrylic acid)-co-methyl methacrylate) and solid dispersion with HPMCAS.

The bioavailability of a therapeutically active compound is generally determined by (i) the solubility/dissolution rate of the compound, and (ii) the partition coefficient/permeability of the compound through a subject's gastrointestinal membrane. The major cause of poor bioavailability of a therapeutically active compound is usually the poor solubility/dissolution rate of said compound. Poor bioavailability is also often accompanied by high variable patient blood levels and unpredictable dose/therapeutic effects due to erratic absorption of the drug by the patient.

As used herein, the term "poorly soluble" when referring to a chemical compound in relation to its solubility in water or an oil, can be defined as in U.S. Pharmacopeia and National Formulary (USP-NF). According to this definition, solubility is stated in terms of the parts of the solvent needed to dissolve one part of the solute. A compound that is sparingly soluble in a particular solvent, such as water, requires 30-100 parts of the solvent to dissolve one part of the compound. A compound that is slightly soluble requires 100-1000 parts of the solvent. A compound that is very slightly soluble requires 1000-10,000 parts of the solvent. A compound that is insoluble (such as Compound A) requires more than 10,000 parts of the solvent to dissolve one part of the solute.

The lack of solubility of such drugs, and the inability to obtain sufficiently high concentrations of drugs in solution in pharmaceutically acceptable carriers, is a serious problem for formulating these drugs and thereof limit the therapeutic benefit that can be achieved for such compounds. Lack of solubility is additionally a concern in the formulation of compounds for various different targets which need significantly high doses and need to establish very high safety margin over the therapeutic effective dose. Accordingly, a significant need existed for a method to increase the solubility of these drugs.

To improve the desired properties of poorly soluble drugs, many technologies have been developed, including but not limited to the following:

1. Salt Formation: This is the most widely used approach to increase solubility of weakly acidic or basic NCE's. (Wadke, D. A. et al, *Pharmaceutical Dosage Forms: Tablets, Vol.* 1, 1989, pp 1-73). The solubility of salt is typically driven by the counter ion and selection of counter-ion is based on many parameters such as solubility, hygroscopicity and stability of the physical form. In spite of the numerous advantages associated with salt forms, developing a stable salt is not always feasible. In many cases, increased dissolution rate is difficult to achieve because of the reconversion of salts into their respective acid or base forms in the physiological environment.

2. Particle size reduction: Due to their poor solubility, the absorption/bioavailability of some compounds is dissolution rate limited. A reduction in particle size improves the dissolution rate significantly, which provides better absorption potential and potentially leads to improved therapeutics. Wet milling (U.S. Pat. No. 5,494,683) and Nano-technology (PCT Int. Appl. WO 2004022100) are two examples of the techniques that can be applied to poorly water soluble drugs. Although these conventional methods have been used commonly to increase dissolution rate of drug, there are practical limitations as the desired bioavailability enhancement may not always be achieved simply by particle size reduction. Also, agglomeration due to increased surface energy or poor wetting can overturn any benefit of reduced particle size.

3. Lipid formulation: Poorly soluble drugs may dissolve in lipid based vehicle at much higher concentration than in aqueous media. After being dosed, the lipid formulation is dispersed in gastric and intestinal fluid, which provides a large surface area for the drug to diffuse from its solution in lipid to the gastric or intestinal fluid. The high solubility of the drug in the lipid formulation provides the strong driving force for the diffusion. Self-emulsifying drug delivery system (SEDDS) is one example. Depending on the selection of the lipid vehicle, the resulting aqueous dispersion may yield very fine or crude emulsion (see e.g. U.S. Pat. Nos. 5,969,160, 6,057,289, 6,555,558 and 6,638,522). Some constraints for these formulation techniques comes from insufficient drug solubility in lipid vehicles, physical in-stability (e.g. polymorph crystallization with reduced solubility), etc.

4. Solid dispersion: In recent years, solid dispersions have attracted attention in the field of oral preparations, especially for the poorly soluble compounds. Solid dispersion technologies involve stabilization of the drug in its amorphous form, within a carrier matrix. The amorphous form allows faster dissolution of the drug and is particularly promising for orally administered drugs (because of the wider choices of carrier matrices). However, to use this technology effectively identification of an appropriate carrier that is compatible with the drug is necessary. Several techniques have been developed to prepare solid dispersions, including co-precipitation (see e.g. U.S. Pat. Nos. 5,985,326 and 6,350,786), fusion/spray-drying (see e.g. U.S. Pat. No. 7,008,640), and hot-melt extrusion (see e.g. U.S. Pat. No. 7,081,255). All these techniques provide a highly dispersed drug molecule in polymer matrix, which improve the dissolution of the drug from the dispersion. The solid dispersions prepared from different methods may differ in properties, such as porosity, surface area, density, stability, hygroscopicity, dissolution and therefore bioavailability. However, there is no evidence in the literature suggesting the superiority of one method over another to achieve the desired pharmacokinetic profile, particularly better dose proportionality.

While some of these techniques are well known, most of them provide a number of unique challenges and can't be applicable to the brick dust like compounds i.e. with very high melting point and practically no solubility in any of the organic solvents.

Furthermore, the amorphous solid dispersions are high energy formulations which present additional challenges since they are, by nature, thermodynamically unstable. Consequently, their successful development depends in good measure on the understanding of the specific interactions responsible for their stabilization (Serajuddin, A. T. M. J. Pharm. Sci. 1999, 88, 1058-1066; Janssens, S. and Van den Mooter, G. J. Pharm. Phamacol. 2009, 61, 1571-1586.). However, there is no universal or reliable method to select neither a technology nor a polymer to have guaranteed amorphous stability and improved bioavailability. Solubility parameters have been reported to aid the selection of the polymers. However, as shown in Table 1 below, the solubility parameters and the rank of them between different polymers are not consistent between different calculations and therefore, different polymers could be selected based on different calculations. Therefore, calculations do not predict any benefit of using one particular polymer over another in terms of providing stable amorphous dispersion.

TABLE 1

Solubility Parameters calculations for Compound A with various polymers

| Drug/Polymer | δ(van Krevelen) | δ(Hansen) | δ(Hoy) |
|---|---|---|---|
| Compound A | 26.3537 | 20.3818 | 26.3537 |
| HPMC-AS | 26.0281 | 40.5648 | ~ |
| KOLLIDON VA 64 ® (Vinylpyrrolidone-vinyl acetate copolymer) | 24.2935 | 25.6482 | 24.3355 |
| PVP (K30, K90) | 25.9657 | 27.6816 | 24.8893 |
| EUDRAGIT L100 ® (Poly(methacrylic acid)-co-methyl methacrylate) | 23.447 | 21.1627 | 20.2345 |
| EUDRAGIT L100-55 ® (Poly(methacrylic acid)-co-methyl methacrylate) | 23.5976 | 20.4951 | 20.5515 |
| EUDRAGIT EPO ® (Poly(butyl methacrylate-co-(2-dimethylaminoethyl) methacrylate-co-methyl methacrylate)) | 20.3652 | 16.68035 | 16.802 |
| SOLUPLUS ® (PVAc-PVCap-PEG) | 19.4651 | 20.2765 | — |

For solid dispersion formulations, if the amorphous re-crystallize, one can speculate that the bioavailability is impacted due to the loss of the advantage from the improved solubility of the amorphous form. However, it is not clear how the drug loading or the polymer plays a role in bioavailability when the amorphous stability is maintained in a wide range of drug loads.

Description of Related Art

Compound A, methods of synthesizing it as well as conventional pharmaceutical formulations containing the compound has been described in WO2011/098398. This patent application describes a method for making the thermodynamically stable form of the compound and the mechanism of action for the molecule.

U.S. Pat. No. 6,350,786 discloses pharmaceutical compositions comprising of amorphous dispersion of various different compounds i.e. Tolcapone, Accutane, Saquinavir and several others, obtained by using micro precipitated bulk Powder (MBP) technology. The MBP technology was found to be widely applicable and several different polymers i.e. EUDRAGIT L100-55® (Poly(methacrylic acid)-co-methyl methacrylate), EUDRAGIT L100® (Poly(methacrylic acid)-co-methyl methacrylate), Hydroxypropylmethylcellulose phthalate (HP-50) or EUDRAGIT S 100® (Poly (methacrylic acid)-co-methyl methacrylate) were found to be successful in generating stable amorphous dispersion for these drugs.

US Patent Application No. US2010/0310659 A1 describes pharmaceutical composition of Propane-1-sulfonic acid {3-[5-(4-chloro-phenyl)-1H-pyrrolo[2,3-b]pyridine-3-carbonyl]-2,4-difluoro-phenyl}-amide with HPMC-AS using MBP technology.

US Patent Application No. US2009/145999 discloses an amorphous composition of Propane-1-sulfonic acid {3-[5-(4-chloro-phenyl)-1H-pyrrolo[2,3-b]pyridine-3-carbonyl]-2,4-difluoro-phenyl}-amide with co-povidone polymer via hot melt extrusion process.

U.S. patent application Ser. No. 12/902,186 specifies a pharmaceutical composition of low melting drug HEP with HPMC-AS using MBP and HME technology, where amorphous dispersion via HME process showed slightly improved pharmacokinetic behavior over MBP formulation.

In U.S. Pat. No. 6,350,786, solid dispersions using water-insoluble ionic polymers with a molecular weight greater than 80,000 D are disclosed to provide a stable amorphous formulation.

U.S. Pat. No. 6,548,555 describes the use of ionic polymers, including hypromellose acetate succinate (HPMCAS), to prepare solid dispersions for improved solubility and better bioavailability.

WO2007/109605 discloses spray dried compositions comprising a drug and, among many other polymers, PVP or PVP-VA.

HPMCAS is a polymer that has been used for the manufacture of solid dispersions of drugs (for example, H. Konno, L. S. Taylor, Journal of Pharmaceutical Sciences, Vol. 95, No. 12, 2006, 2692-2705). Other polymers as used herein, in particular Povidone (PVP, Kollidon®) and Kollidon® VA 64 (Poly(vinylpyrrolidone-co-vinyl acetate) (6+4); Copovidone or PVP VA 64) are commercially available, for example from BASF SE (67056 Ludwigshafen, Germany).

Kondo et al showed improved oral absorption of poorly soluble drugs in enteric co-precipitates (e.g. J Pharm Sciences, 83(4) 1994). The polymer used in this preparation was hypromellose phthalate and the co-precipitates were prepared by solvent evaporation method followed by drying at 80° C. Based on dissolution data, such co-precipitates systems solubilized by co solvents or solid dispersion approaches, may revert back to crystalline form, resulting in loss of bioavailability at higher dose.

While micro co-precipitation has been utilized for the stabilization of several drug substances in the solid state, it may not be necessary to satisfactorily tailor the pharmacokinetic profile of such poorly soluble compounds, particularly the close dependent exposure, which is very important to manage the safety and efficacy of the compound. These supersaturated formulations may revert back to crystalline form upon storage or under stress conditions, resulting in loss of bioavailability. The polymer and process selection for amorphous dispersion found to play critical role in stabilizing those dispersion. However, there is no absolute method to a priori judge whether a given polymer or process will provide adequate stability of the amorphous dispersion.

The drug loading in solid amorphous formulation has been found to be critical. It is usually the lower the drug load, the better the stability. Above certain drug loading, the amorphous solid dispersion poses high risk in re-crystallization during shelf life and therefore diminishes the benefit of the improved solubility and bioavailability. Lin and Cham (C. W. Lin, T. M. Cham. Effect of particle size on the available surface area of nifedipine from nifedipine-polyethylene glycol 6000 solid dispersions. Int. J. Pharm., 127 (1996), pp. 261-272) showed that solid dispersions of naproxen in PEG 6000 released drug faster when a 5 or 10% naproxen loading was used than when a 20, 30 or 50% loading was used. These results could be explained on the basis of X-ray diffraction results, which indicated that dispersions with low loading levels of naproxen were amorphous whereas those with high loadings were partly crystalline (Dissolution Improvement of High Drug-loaded Solid Dispersion. AAPS Pharm Sci Tech 2006; 7 (2) Article 52). An obstacle of solid dispersion technology in pharmaceutical product development is that a large amount of carrier, i.e. more than 60% to 90% wt/wt, was required to achieve the desired dissolution. This high percentage of carrier warrants consistency of product performance at the time of manufacturing and during shelf storage.

The present invention relates to stabilized solid dispersions of Compound A which are characterized by an enhanced dissolution rate and significantly improved bioavailability. In one embodiment, the present solid dispersions are prepared by micro-precipitation, leading to said solid dispersion as micro-precipitated bulk powder (MBP). In another embodiment, the present solid dispersions are prepared by spray-drying (SD) processes. Depending on the process, different polymers may be used to effectively immobilize Compound A in said solid dispersion.

A polymer screening has been carried out using the following polymers:
Hydroxypropyl methylcellulose (HPMC 2910, E5)
Hydroxy propyl cellulose HPC LF
Povidone K30 (PVP K30)
COPOVIDONE (Poly(vinylpyrrolidone-co-vinyl acetate) (6+4) or PVP VA 64)
EUDRAGIT EPO® (Poly(butyl methacrylate-co-(2-dimethylaminoethyl) methacrylate-co-methyl methacrylate))(cationic copolymer based on dimethylaminoethyl methacrylate, butyl methacrylate, and methyl methacrylate)
SOLUPLUS® (PVAc-PVCap-PEG)
HPMCAS, LF The following weight ratios of Compound A:Polymer were tested: 70% A:30% Polymer; 50% A:50% Polymer; 30% A:70% Polymer; and 50% A:45% Polymer:5% DOSS (Dioctyl sodium sulfosuccinate or docusate sodium). In addition, the following polymers were tested in a weight ratio 50% A:50% Polymer; and 30% A:70% Polymer:
Povidone 12 PF (PVP 12 PF)
Povidone 17 PF (PVP 17 PF)
Povidone K25 (PVP K25)
Povidone K30 (PVP K30)
Povidone K90 (PVP K90)
COPOVIDONE (Poly(vinylpyrrolidone-co-vinyl acetate) (6+4))
EUDRAGIT EPO® (Poly(butyl methacrylate-co-(2-dimethylaminoethyl) methacrylate-co-methyl methacrylate))(cationic copolymer based on dimethylaminoethyl methacrylate, butyl methacrylate, and methyl methacrylate)
SOLUPLUS® (PVAc-PVCap-PEG)
HPMCAS, LF It has been demonstrated that among the various polymers tested, HPMCAS, Povidone (PVP) and COPOVIDONE (Poly(vinylpyrrolidone-co-vinyl acetate) (6+4)) show improved dissolution profiles for Compound A. Improved dissolution profiles mean an improved release of Compound A from the solid dispersion formed by that compound and the respective polymer. Additionally, the use of Povidone or COPOVIDONE (Poly(vinylpyrrolidone-co-vinyl acetate) (6+4) or PVP VA 64) can lead to dissolution profiles which are independent from the pH-value in the dissolution environment. Therefore, dissolution and thus release of Compound A from a solid dispersion formed with Povidone or COPOVIDONE (Poly(vinylpyrrolidone-co-vinyl acetate) (6+4)) may already take place early after oral administration of such solid dispersion, for example in the stomach. This early dissolution/release of Compound A may therefore significantly improve the bioavailability of Compound A.

As used herein, the term solid dispersion means any solid composition having at least two components. In certain embodiments, a solid dispersion as disclosed herein includes an active ingredient (for example Compound A); preferably dispersed among at least one other component, for example a polymer. In certain embodiments, a solid dispersion as disclosed herein is a pharmaceutical dispersion that includes at least one pharmaceutically or biologically active ingredient (for example Compound A). In some embodiments, a solid dispersion includes Compound A molecularly dispersed with a polymer. Preferably the solid dispersion is a one phase system. An especially preferred solid dispersion according to the present invention is microprecipitated bulk powder (MBP) comprising Compound A. In another embodiment, the solid dispersion is obtained by spray-drying and comprises Compound A and, as polymer, COPOVIDONE (Poly(vinylpyrrolidone-co-vinyl acetate) (6+4)).

The term "molecularly dispersed", as used herein, refers to the random distribution of a compound (e.g., Compound A) with a polymer. In certain embodiments the compound is present in the polymer in a final state of subdivision. See, e.g., M. G. Vachon et al., *J. Microencapsulation*, 14:281-301 (1997) and Vandelli et al., *J. Microencapsulation*, 10: 55-65 (1993). In some embodiments, a compound (for example, Compound A) may be dispersed within a matrix formed by the polymer in its solid state such that the compound is immobilized in its amorphous form. Whether a compound is molecularly dispersed in a polymer may be evidenced in a variety of ways, e.g., by the resulting solid molecular complex having a single glass transition temperature, or the absence of signals indicating any crystalline amounts of said compound (e.g. Compound A) in X-ray diffraction curves.

The term "solid molecular complex" as used herein means a solid dispersion that includes Compound A molecularly dispersed within a polymer matrix.

The term "immobilize", as used herein with reference to the immobilization of the active compound in the polymer matrix, means that molecules of the compound interact with molecules of the polymer in such a way that the molecules of the compound are held in the aforementioned matrix and prevented from crystal nucleation due to lack of mobility. In some embodiments the polymer may prevent intermolecular hydrogen bonding or weak dispersion forces between two or more drug molecules of Compound A. See, for example, Matsumoro and Zografi, Pharmaceutical Research, Vol. 16, No. 11, p 1722-1728, 1999.

Percentages (%) as used herein are expressed in weight percent (weight %, wt/wt), unless explicitly otherwise stated.

Accordingly, in a first aspect, provided is a solid dispersion that includes Compound A and a polymer. Also provided is a solid molecular complex that includes Compound A and a polymer. The polymer may be a non-ionic polymer or an ionic polymer. In certain embodiments, the polymer is selected from the group consisting of hydroxypropylmethyl cellulose acetate succinate (HPMCAS), hydroxypropylmethyl cellulose, methacrylic acid copolymers, and the like, as well as mixtures of any two or more thereof. In a preferred embodiment, the polymer is selected from HPMCAS or Povidone (PVP, KOLLIDON®) or COPOVIDONE (Poly(vinylpyrrolidone-co-vinyl acetate) (6+4); KOLLIDON® VA 64; PVP VA 64).

The stable solid dispersion comprises from about 10% to about 90%, in certain embodiments from about 30% to about 70%, or from about 40% to about 60%, or from about 20% to about 50%, or from about 50% to about 70% (wt/wt) of Compound A molecularly dispersed in a matrix formed by a polymer. In certain embodiments this polymer is hypromellose acetate succinate (HPMCAS), or Povidone (PVP), or COPOVIDONE (Poly(vinylpyrrolidone-co-vinyl acetate) (6+4)). Most preferably the stabilized amorphous dispersion composition of Compound A of the present invention comprises no significant amounts of crystalline Compound A, as demonstrated by amorphous X-ray powder diffraction (XRPD) of said compositions.

The active ingredient (i.e. Compound A) has the chemical name of 4-{[(2R, 3S, 4R, 5S)-4-(4-Chloro-2-Fluoro-Phenyl)-3-(3-Chloro-2-Fluoro-Phenyl)-4-Cyano-5-(2,2-Dimethyl-Propyl)-Pyrrolidine-2-Carbonyl]-Amino}-3-Methoxy-Benzoic Acid, (Compound A) and can be represented by the following structural formula:

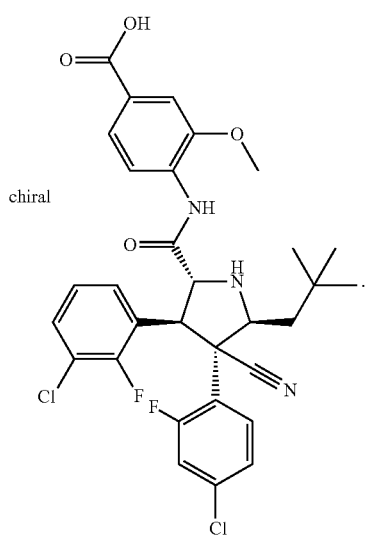 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

The crystalline form of Compound A (herein sometimes referred to as "drug", "API") has a melting point of approximately 277° C. and possess very low aqueous solubility (<0.05 µg/ml) at physiological pHs (from pH 1.5-7.0), consequently very low bioavailability. The permeability of the compound is not high as determined with the Caco-2 assay value of $0.8 \times 10^{-6}$ cm/s. The poor solubility and the targeted high doses/frequency of dosing for this series of compounds led to the categorization of Compound A as BCS class IV compound (poor solubility/poor permeability).

Compound A, as well as methods for making it, is for example disclosed in U.S. Pat. No. 8,354,444 and WO2011/098398. More specifically, Compound A has the potential to treat a variety of proliferative disorders, such as e.g. cancer, due to its ability to inhibit the MDM2-p53 interaction. The term "cancer" as used herein means solid—and hematological tumors, selected from the group consisting of breast cancer, prostate cancer, cervical cancer, ovarian cancer, gastric cancer, colorectal cancer (i.e. including colon cancer and rectal cancer), pancreatic cancer, liver cancer, brain cancer, neuroendocrine cancer, lung cancer, kidney cancer, hematological malignancies (e.g. leukemia), melanoma and sarcomas. More especially preferably the cancer is selected from the group consisting of hematological malignancies, prostate cancer, breast cancer, cervical cancer, ovarian cancer, colorectal cancer, melanoma and lung cancer. In an especially preferred embodiment the cancer is acute myeloid leukemia (AML), or prostate cancer.

In one embodiment, the present invention provides a physically stable solid dispersion comprising a compound having an aqueous solubility of less than 1 µg/ml and a melting point of >270° C. together with a stabilizing polymer.

In another embodiment, the present invention provides the solid dispersion as disclosed above wherein the compound having an aqueous solubility of less than 1 µg/ml is 4-{[(2R, 3S, 4R, 5S)-4-(4-Chloro-2-Fluoro-Phenyl)-3-(3-Chloro-2-Fluoro-Phenyl)-4-Cyano-5-(2,2-Dimethyl-Propyl)-Pyrrolidine-2-Carbonyl]-Amino}-3-Methoxy-Benzoic Acid (Compound A).

In another embodiment, the present invention provides the solid dispersion as disclosed above, wherein the stabilizing polymer is hypromellose acetate succinate (HPMCAS).

In another embodiment, the present invention provides the solid dispersion as disclosed above wherein the stabilizing polymer is EUDRAGIT® L-100 or EUDRAGIT L100-55® (Poly(methacrylic acid)-co-methyl methacrylate).

In another embodiment, the present invention provides the solid dispersion as disclosed above, wherein the stabilizing polymer is Povidone (PVP) or COPOVIDONE (Poly(vinylpyrrolidone-co-vinyl acetate) (6+4)).

In another embodiment, the present invention provides any of the solid dispersions as disclosed above wherein the ratio of the amount by weight of the Compound A within the solid dispersion to the amount by weight of the stabilizing polymer therein is between 5:95 to 70:30.

In another embodiment, the present invention provides any of the solid dispersions as disclosed above wherein the ratio of the amount by weight of the Compound A within the solid dispersion to the amount by weight of the stabilizing polymer therein is preferably 30:70 to 50:50.

In yet another embodiment, the solid dispersion according to the present invention is obtained by spray drying a solution of COPOVIDONE (Poly(vinylpyrrolidone-co-vinyl acetate) (6+4)) and Compound A. Any solvent wherein both, COPOVIDONE (Poly(vinylpyrrolidone-co-vinyl acetate) (6+4)) and Compound A are soluble can be used. Preferably, 50% (by weight) COPOVIDONE (Poly(vinylpyrrolidone-co-vinyl acetate) (6+4)) and 50% (by weight) Compound A are dissolved in acetone. The combined amount of COPOVIDONE (Poly(vinylpyrrolidone-co-vinyl acetate) (6+4))+Compound A represents 3-7%, preferably 5% (by weight), of the acetone solution. This solution is spray dried by conventional spray dried methods, followed by a secondary drying process. All conventional secondary drying methods can be used, preferably a tray dryer, a screw dryer or a fluid bed dryer. The so obtained spray dried powder is further characterized by a particle size distribution from about $d_{10}=5$ to 10 μm, $d_{50}=10$ to 20 μm and $d_{90}=30$ to 60 μm (measured by laser diffraction), and a bulk density of 01.0 to 0.30 g/cm$^3$.

The solid dispersion, in particular the MBP and/or spray-dried products obtainable according to the methods provided, can be used in a wide variety of forms for administration of drugs that are poorly water soluble, such as Compound A, and in particular for oral dosage forms. Exemplary dosage forms include powders or granules that can be taken orally either dry or reconstituted by addition of water to form a paste, slurry, suspension or solution; tablets, capsules, or pills. Various additives can be mixed, ground or granulated with the solid dispersion as described herein to form a material suitable for the above dosage forms. Potentially beneficial additives may fall generally into the following classes: other matrix materials or diluents, surface active agents, drug complexing agents or solubilizers, fillers, disintegrants, binders, lubricants, and pH modifiers (e.g., acids, bases, or buffers). Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, and croscarmellose sodium. Examples of binders include methyl cellulose, microcrystalline cellulose, starch, and gums such as guar guru, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. At least one function of inclusion of such pH modifiers is to control the dissolution rate of the drug, matrix polymer, or both, thereby controlling the local drug concentration during dissolution.

Additives may be incorporated into the solid amorphous dispersion during or after its formation. In addition to the above additives or excipients, use of any conventional materials and procedures for formulation and preparation of oral dosage forms using the compositions disclosed herein known by those skilled in the art are potentially useful.

Therefore, in another embodiment, there is provided a unit dose solid formulation, preferably a tablet, comprising a solid dispersion according to the present invention together with commonly used pharmaceutical ingredients selected from the group consisting of disintegrants, diluents, lubricants, glidants together with a film coat.

In another embodiment, the present invention provides a unit dose solid formulation comprising approximately 80% of any of a solid dispersion according to the present invention together with about 7% croscarmellose sodium, about 6.8% mannitol, about 4% crospovidone, about 1.5% colloidal silicon dioxide and about 0.7% of magnesium stearate which is then encapsulated or compressed and coated as tablet.

In yet another embodiment, the present invention provides a unit dose solid formulation, characterized in that a solid dispersion obtained by spray drying of the Compound A together with COPOVIDONE (Poly(vinylpyrrolidone-co-vinyl acetate) (6+4)) representing about 80% wt/wt of the kernel weight is further blended with a filler (6.8% up to 10.8% of kernel weight), preferably selected from mannitol, microcrystalline cellulose, lactose monohydrate or silicon dioxide; one or two disintegrants (4% wt/wt of kernel weight) selected from croscarmellose sodium or crospovidone; a glidant (1% wt/wt of kernel weight) preferably colloidal silicon dioxide; and a lubricant (0.2% wt/wt of kernel weight) magnesium stearate, using a tumble mixer.

In yet another embodiment, there is provided the specific tablet formulation according to Example 16.

In another embodiment, the present invention provides a method for preparing a solid dispersion of a compound having an aqueous solubility of less than 1 μg/ml, preferably Compound A, and an ionic polymer which comprises Banning a solution of the compound and the polymer in dimethyl-acetamide, or any other suitable solvent and co-precipitating the drug with the polymer using anti-solvent. Preferably the polymer in this embodiment is HPMCAS.

In another embodiment, the present invention provides a method for preparing a solid dispersion of a compound having an aqueous solubility of less than 1 μg/ml, preferably Compound A, and an ionic polymer which comprises forming a solution of the compound and the polymer in acetone, or any other suitable solvent, and spray drying the drug with the polymer. Preferably the polymer in this embodiment is selected from Povidone (PVP) or COPOVIDONE (Poly(vinylpyrrolidone-co-vinyl acetate) (6+4)).

In another embodiment, the present invention provides a pharmaceutical preparation comprising a solid dispersion according to the present invention together with additional pharmaceutically acceptable adjuvants.

In another embodiment, the present invention provides a solid dispersion according to the present invention for use as a medicament for the treatment of cancer, in particular AML or prostate cancer.

In another embodiment, the present invention provides the use of a solid dispersion according to the present invention for the manufacture of a medicament for the treatment of cancer, in particular AML or prostate cancer.

Extremely low solubility/bioavailability pose challenges to attaining desirable exposure and safety margins for Compound A. Since the low bioavailability of hydrophobic drugs with extremely low water solubility can be a serious problem, different approaches have been explored to achieve the desirable high levels of drug solubility and dissolution rate. These approaches will now be further illustrated by the following examples which are not intended to limit the scope of the invention.

EXAMPLES

A.: Crystalline Formulation Approaches

Below are the details (example 1) of various different formulation approaches with crystalline form or salt form of the compound. Table 1 illustrates the relative bio-availability obtained with those formulation approaches.

The crystalline formulations were produced as follows:

Example 1: Crystalline Micron-Suspension

Crystalline suspension was prepared by dispersing the crystalline Compound A in aqueous based vehicle consisting 2% hydroxypropylcellullose, 0.15% polysorbate 80, 0.09% methylparaben and 0.01% of propylparaben. The suspension was milled to achieve the median particle size of <10 μm ($d_{0.5}$).

TABLE 2

Bioavailability improvement in monkeys

| Parameters | Units | IV | PO | PO |
|---|---|---|---|---|
| Dose | mg/kg | 1.25 | 30 | 30 |
| Formulation | | | | Crystalline Micron-Crystalline Suspension |
| Food | | Fed | Fed | Fed |
| AUC (0-t*) | μg · hr/mL | 12.8 | 15.8 | 35.0 |
| AUC extrap | μg · hr/mL | 12.9 | 16.1 | 35.5 |
| % AUC Extrap | % | 0.7 | 1.8 | 1.4 |
| AUC/Dose | hr · μg/mL/mg/kg | 10.3 | 0.5 | 1.2 |
| Oral Cmax | μg/mL | | 1.1 | 1.7 |
| Bioavailability | | | 5.2% | 11.5% |

Example 2: Salt Based Suspension

Figure 3:
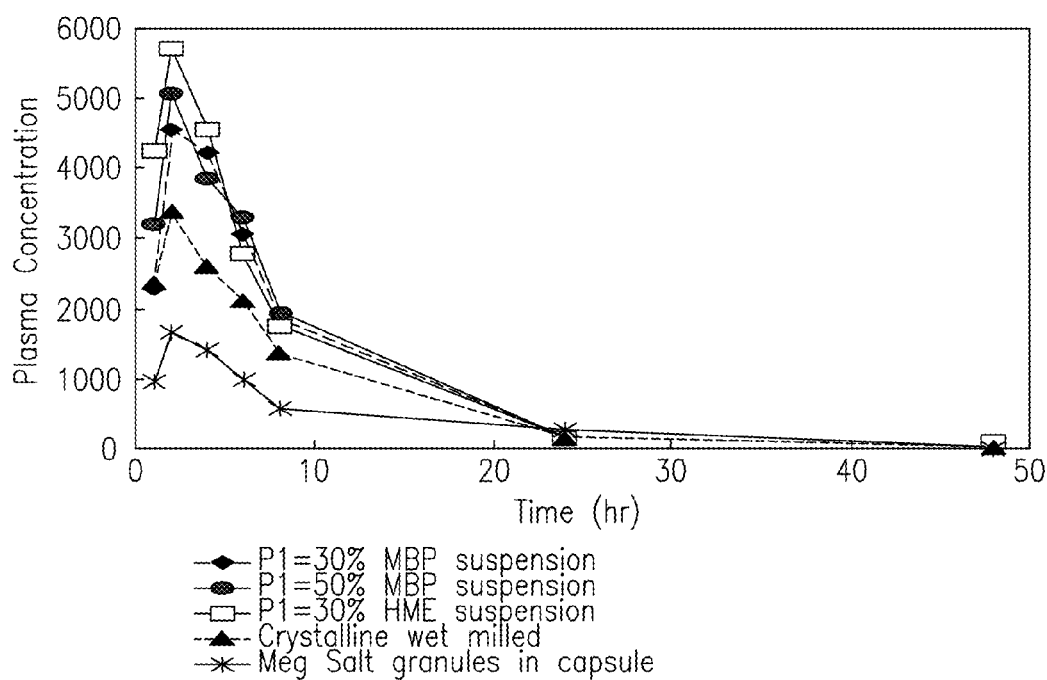
FIG. 3 illustrates the plasma concentrations of compound A versus time profile dosed as: P1-suspension dosage form of amorphous solid dispersion as MBP at 30% drug load with HPMCAS; P2-suspension dosage form of amorphous solid dispersion as MBP at 50% drug load with HPMCAS; P3-suspension dosage form of amorphous prepared by HME with PVPVA64 at 30% drug load; P4-crystalline micron suspension; P5-capsule dosage form filled with granules of compound A as Meglumine salt.
Figure 4:
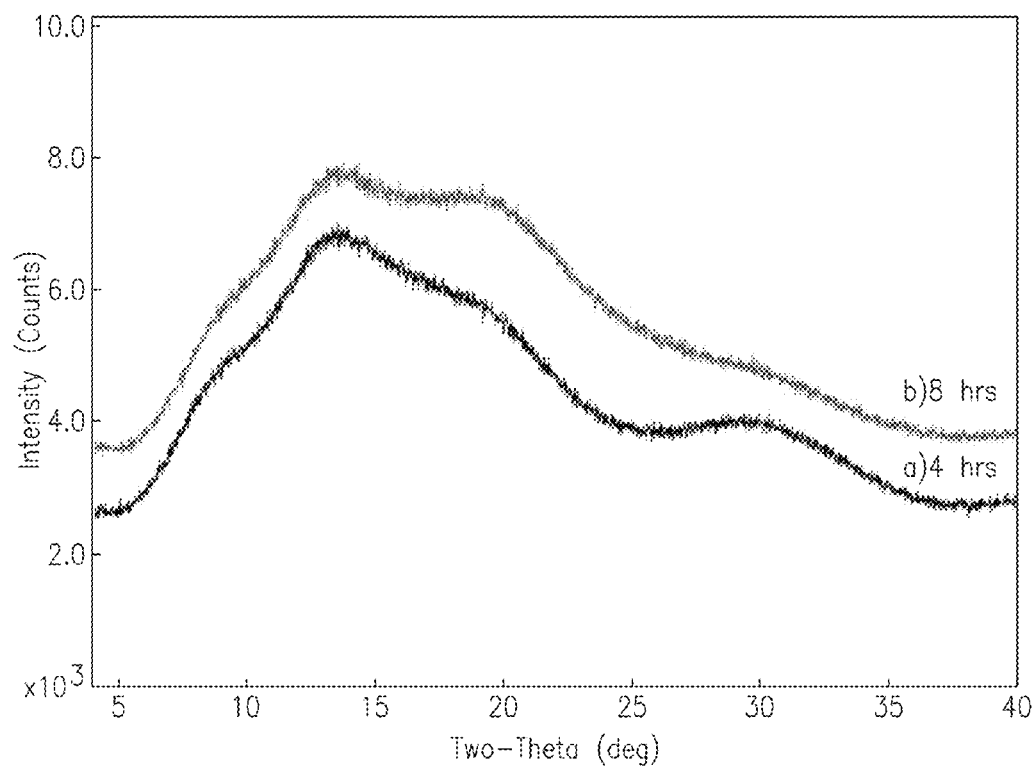
FIG. 4 illustrates the stability of the amorphous solid dispersion in X-ray powder diffraction (XRPD) graph. The solid dispersion (50% drug load with HPMCAS polymer) remained as amorphous after a) 4 hours and b) 8 hours treatment at 70° C.

Salt screening had identified several potential salts of Compound A (see Table 3 below). Among them, Meglumine was a promising salt with the most improved aqueous solubility and was therefore tested in an animal pharmacokinetics study in solid dosage form in capsule containing Compound A meglumine salt as granules with poloxamer 188, crospovidone, colloidal silica and magnesium stearate. The bioavailability (exposure) was not improved (FIG. 3)

TABLE 3

Solubility of Various Salts of Compound A.

| Compound A Salt | Solubility (μg/mL) | pH |
|---|---|---|
| Sulfate | <0.02 | 2.6 |
| p-Toluenesulfonic acid | <0.02 | 2.7 |
| Sodium | 0.7 | 7.2 |
| Benzenesulfonate acid | <0.02 | 2.4 |
| Meglamine | >1400 | 7.8 |
| Potassium | 0.5 | 8.0 |
| Methanesulfonic acid (Mesylate) | <0.04 | 3.1 |

Amorphous Solid Dispersion Formulation Approaches

It was found that amorphous solid dispersion of Compound A exhibited significantly higher bioavailability than crystalline or salt form of the compound.

Various available technologies were evaluated to generate the suitable amorphous formulation i.e. spray drying, hot melt extrusion, and microprecipitated bulk powder technology, as shown in examples 3-10.

The various carriers which were explored include, hypromellose, hypromellose acetate succinate, KOLLIDON® (Vinylpyrrolidone-vinyl acetate copolymer), KOLLIDON VA 64® (Vinylpyrrolidone-vinyl acetate copolymer), SOLUPLUS® (PVAc-PVCap-PEG), copolymers of acrylic and methacrylic acid, such as EUDRAGIT L100-55® (Poly(methacrylic acid)-co-methyl methacrylate), EUDRAGIT L100® (Poly(methacrylic acid)-co-methyl methacrylate), EUDRAGIT EPO® (Poly(butyl methacrylate-co-(2-dimethylaminoethyl) methacrylate-co-methyl methacrylate)) etc. The experiments were done at various drug loadings ranging from 5%-70%.

Example 3: Amorphous Dispersion Using HME Technology

Compound A, COPOVIDONE (Poly(vinylpyrrolidone-co-vinyl acetate) (6+4)) (or SOLUPLUS® (PVAc-PVCap-PEG), HPMCAS), with or without docusate sodium were melted using a hot melt extruder at 120° C. to 180° C. at drug loading of 30% to 50%. The milled extrudates with COPOVIDONE (Poly(vinylpyrrolidone-co-vinyl acetate) (6+4)) was tested in animal with the following composition: 30% Compound A, 68.75% of COPOVIDONE (Poly(vinylpyrrolidone-co-vinyl acetate) (6+4)), 1% Docusate sodium, and 0.25% colloidal silicon dioxide. The final constituted dosing suspension concentration was 1 mg/mL of Compound A.

Example 4-10: Amorphous Dispersion Using MBP Technology

The drug and polymer (HPMCAS or Eudragit L100) were dissolved in the dimethyl-acetamide (DMA) by stirring at room temperature. The solution with or without filtration was then added to the cold, temperature-controlled antisolvent aqueous media (dilute HCl, around pH 3.0, temperature of 1° C. to 10° C.) that allows rapid co-precipitation of the drug and the polymer. The residual DMA was extracted with frequent washing with cold acidic water and cold water, followed by separation of the wash and the wet precipitate and drying of the precipitate. The dried powder is the so-called MBP subjected to further processing to dosing suspension or tablets. All of the formulations below showed amorphous XRD pattern. (FIG. 1)

TABLE 4

Bioavailability improvement from amorphous solid dispersion formulation with HPMCAS in rats and monkeys.

| | Micron-suspension (crystalline) | MBP Suspension (amorphous) |
|---|---|---|
| Rat (100 mg/kg) | 36% | >100% |
| Monkey (30 mg/kg) | 11.5% | 17.4% |

Example 4 (Amorphous Solid Dispersion with EUDRAGIT L100® (Poly(Methacrylic Acid)-Co-Methyl Methacrylate)): MBP with EUDRAGIT L100® (Poly(Methacrylic Acid)-Co-Methyl Methacrylate at 30% Drug Load Compound A as amorphous solid dispersion (MBP), powder for constitution containing 30% Compound A and 70% EUDRAGIT L100® (Poly(methacrylic acid)-co-methyl methacrylate) polymer. The final dosing concentration was equivalent to 6 mg/mL of Compound A in aqueous vehicle containing 2% w/w hydroxypropylcellulose, 0.1% polysorbate 80 and 0.09% methylparaben and 0.01% propylparaben.

(FIG. 2)

Example 5: Amorphous Solid Dispersion of Compound A with HPMCAS at 30% Drug Load Compound A as amorphous solid dispersion by coprecipitation (MBP) at 30% drug load with 70% HPMC-AS polymer. The final constituted dosing suspension concentration was 1 mg/ml of Compound A in aqueous vehicle containing 2% w/w hydroxypropylcellulose, 0.1% polysorbate 80 and 0.09% methylparaben and 0.01% propylparaben.

Example 6: Amorphous Solid Dispersion of Compound A with HPMCAS at 50% Drug Load Compound A as amorphous solid dispersion (MBP) containing 50% Compound A and 50% HPMC-AS polymer. The MBP was then constituted to a dosing suspension at concentration of 1 mg/mL of Compound A in aqueous vehicle containing 2% w/w hydroxypropylcellulose, 0.1% polysorbate 80 and 0.09% methylparaben and 0.01% propylparaben. (FIG. 3)

Example 7: Amorphous Solid Dispersion of Compound A with HPMCAS at 70% Drug Load Compound A as amorphous solid dispersion (MBP), powder for constitution containing 70% Compound A and 30% HPMC-AS polymer. Suspension concentration upon constitution was 4 mg/mL.

Example 8: Amorphous Solid Dispersion of Compound A with HPMCAS at 50% Drug Load in Tablet Dosage Form Amorphous MBP solid dispersion of Compound A containing 50% Compound A and 50% HPMC-AS was further processed to tablets. The composition was 92.8% of Compound A as amorphous solid dispersion (MBP), with 5% croscarmellose sodium, 1.5% colloidal silicon dioxide, and 0.7% of magnesium stearate.

Example 9: Amorphous Solid Dispersion of Compound A with HPMCAS at 30% Drug Load in Tablet Dosage Form Amorphous solid dispersion of Compound A containing 30% Compound A and 70% HPMC-AS was further processed to tablets. The tablets consisted of 94% of Compound A (30% Compound A and 70% HPMC-AS) as amorphous solid dispersion (MBP), with 3.7% croscarmellose sodium, 1.2% colloidal silicon dioxide, 0.5% hydroxypropyl cellulose, and 0.6% of magnesium stearate.

Example 10: Amorphous Solid Dispersion of Compound A with HPMCAS at 50% Drug Load in Tablet Dosage Form Amorphous solid dispersion MBP of Compound A containing 50% Compound A and 50% HPMC-AS was further processed to tablets. The tablets consisted of 80% of MBP (50% Compound A and 50% HPMC-AS) as amorphous solid dispersion, with 7% croscarmellose sodium, 6.8% mannitol, 4% crospovidone, 1.5% colloidal silicon dioxide, and 0.7% of magnesium stearate. The tablet kernels can then be coated with a conventional aqueous film coating mixture.

Example 11: Solubility Enhancement from Amorphous Solid Dispersion

Approximately 5 mg of Compound A as MBP was placed in 20 mL of 37° C. bio-relevant fluids (Fasted State Simulated Intestinal Fluid and Fed State Simulated Intestinal Fluid) and was filtered through a 0.2 µm filter over time. The filtrate was then analyzed by HPLC.

TABLE 5

Solubility enhancement

| Solvent | Solubility Crystalline Form | MBP (Amorphous) |
|---|---|---|
| FaSSIF | 2 µg/mL | 5 µg/mL |
| FeSSIF | 3 µg/mL | 15 µg/mL |

Example 12: Stability of MBP at High Temperature (Showing Powder XRPD Patterns)

(FIG. 4)

Example 13: Evidence of Stable Amorphous Solid Dispersion

Figure 5:
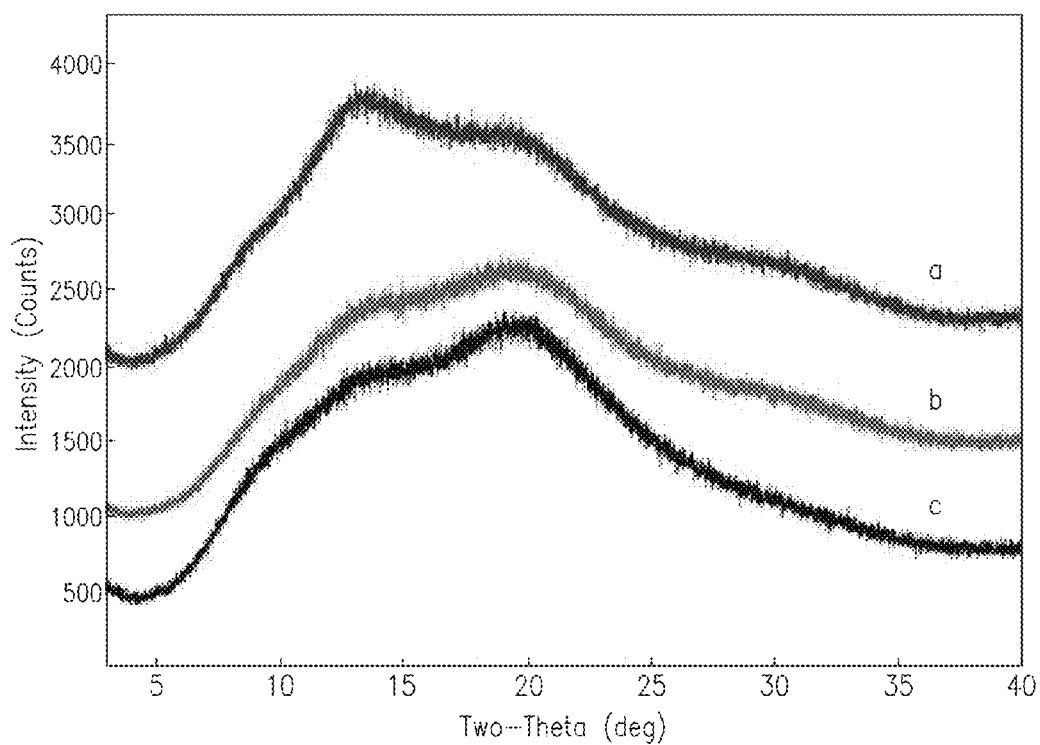
FIG. 5 illustrates the stability of the amorphous solid dispersion in X-ray powder diffraction (XRPD) graph. The MBP at 50% drug load with HPMCAS polymer as amorphous: a) initial, b) 6-month at 40° C./75% RH, c) 6-month at 25° C./60% RH.

As showing in the X-ray powder diffraction (XRPD) that the MBP remained as amorphous after 6-month storage at 25° C./60% RH and 6-month at 40° C./75% RH. (FIG. 5)

Example 14

Figure 6A:
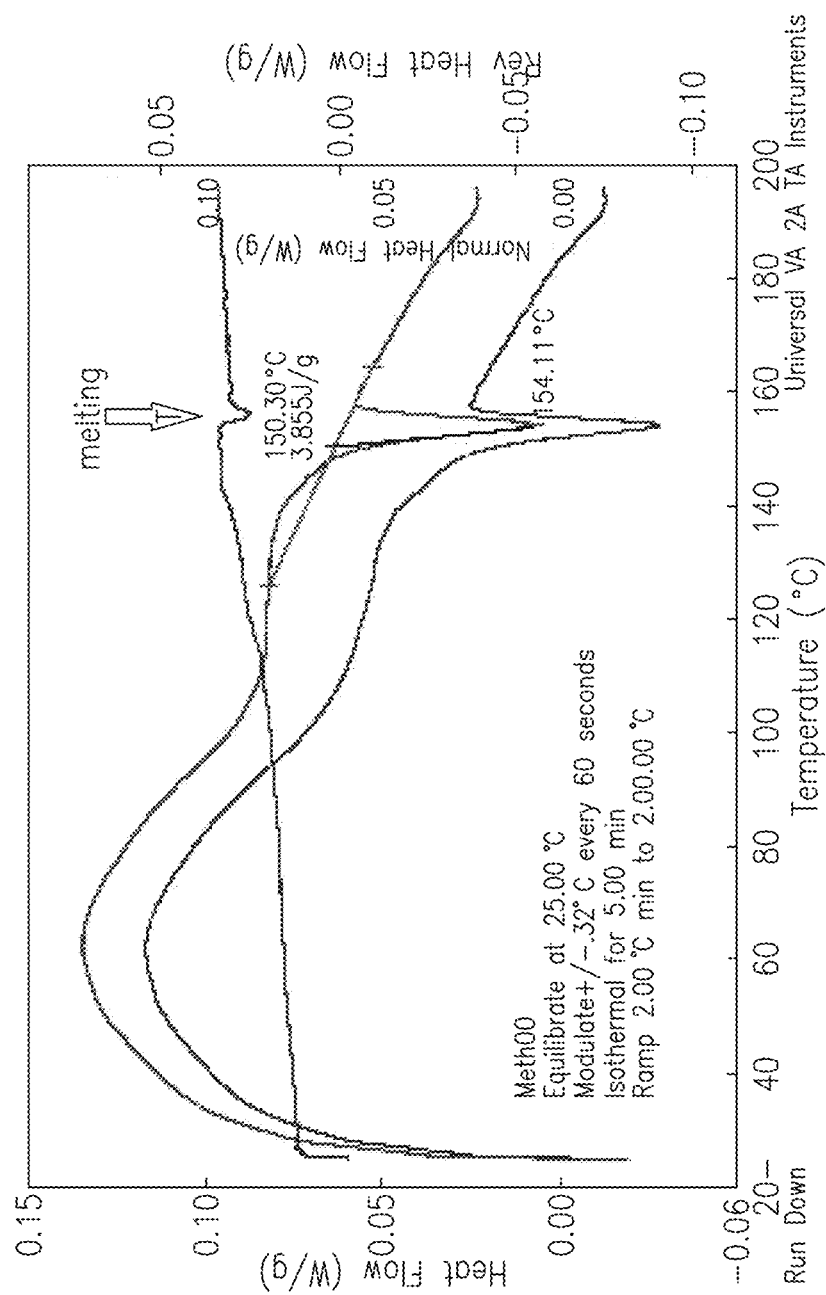
FIGS. 6A and B compare the stability of the MBP to the physical mixture of the amorphous API and polymer at the same ratio using differential scanning calorimetry (DSC) heating cycling method. A) Physical mixture showed melting. B) MBP showed glass transition (Tg).
Figure 6B:
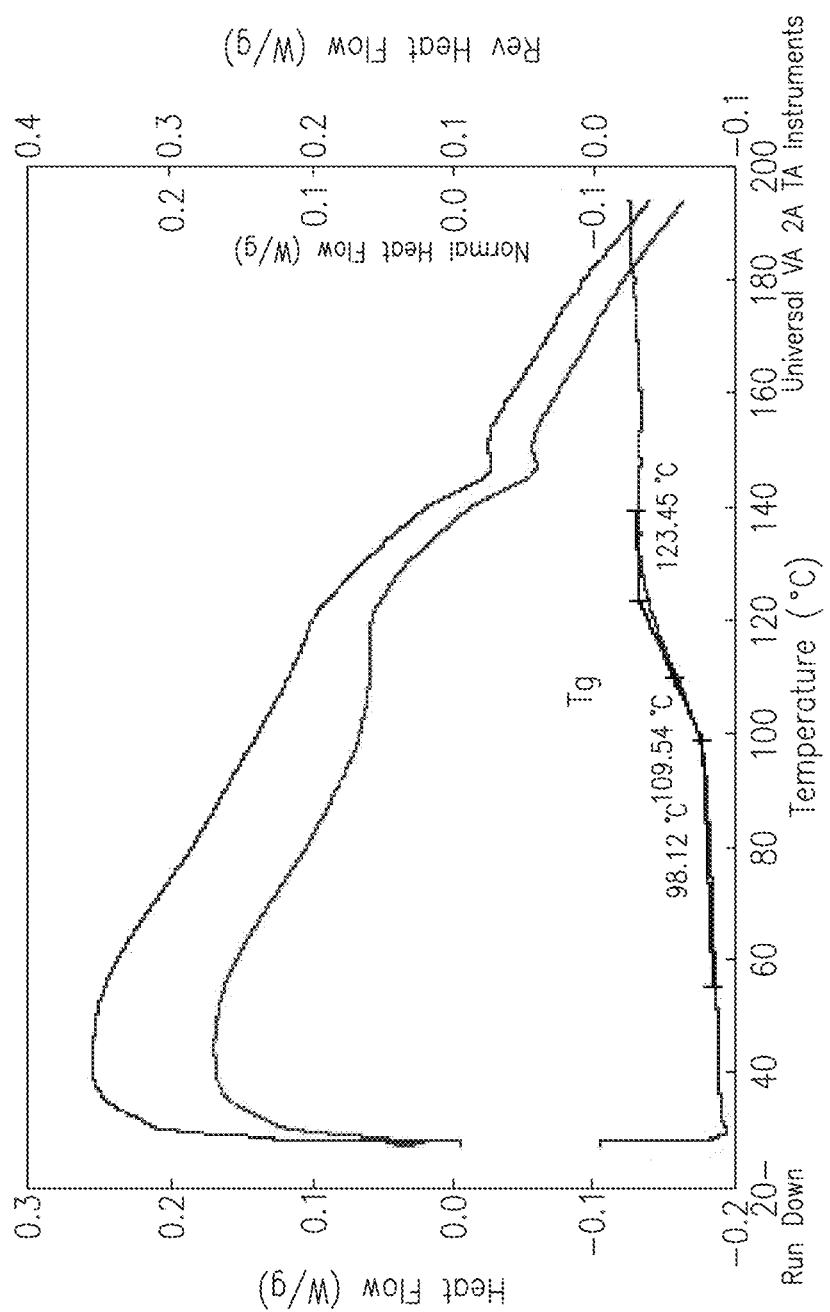

Comparing the amorphous MBP solid dispersion to the physical mixture of the same components using differential scanning calorimetry (DSC) heating cycling method showed that the physical mixture crystalized while MBP remained amorphous.
(FIG. 6)

Example 15

Figure 7:
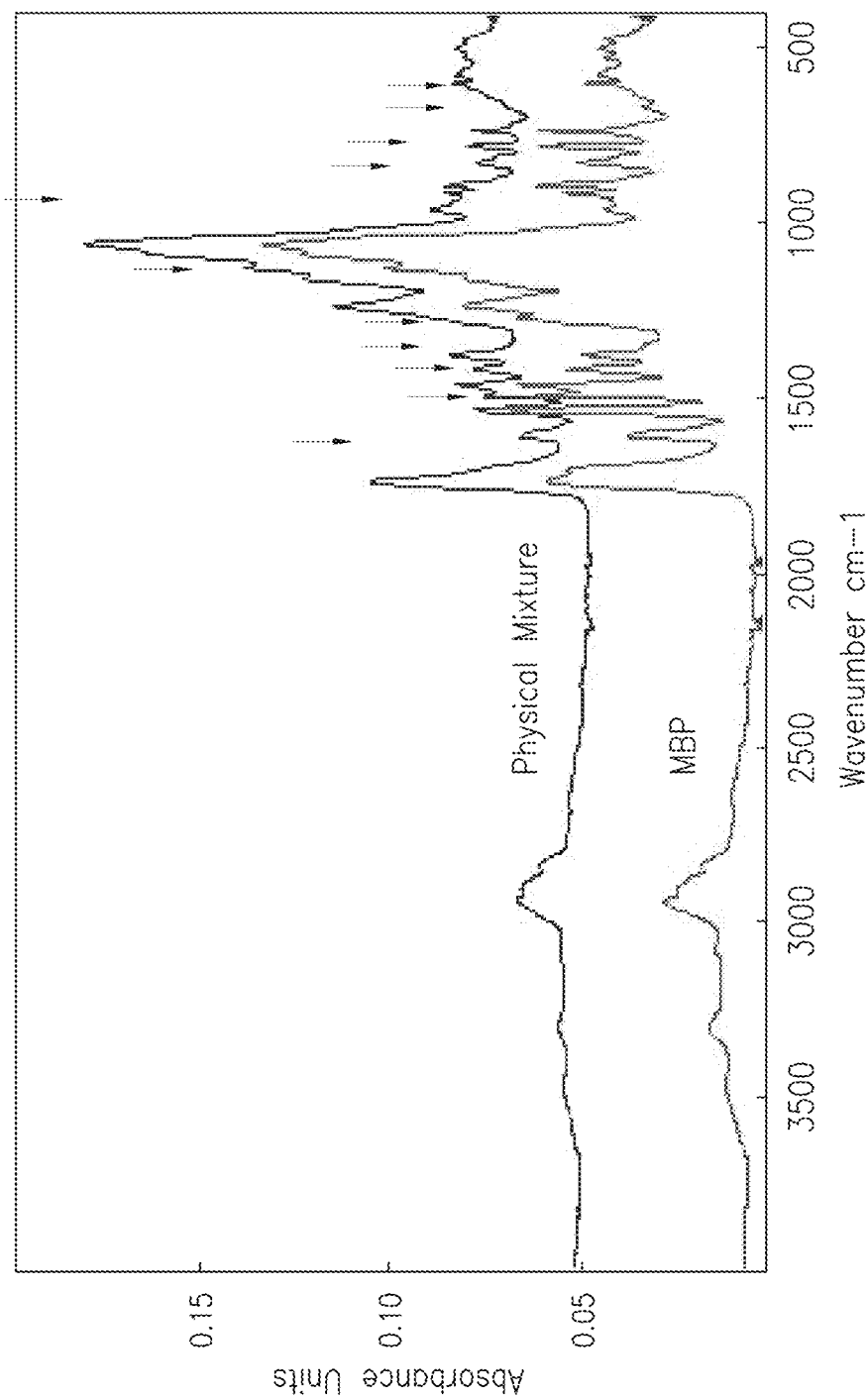
FIG. 7 illustrates the interactions between the drug and the polymer in the MBP using FTIR (Fourier Transform Infrared) Spectroscopy. a) physical mixture b) MBP.

FTIR (Fourier Transform Infrared) Spectroscopy illustrated (FIG. 7) that in MBP the drug and polymer are molecularly dispersed providing greater stability and not prone to crystallization. On the other hand Amorphous API in physical mixture is not molecularly dispersed and therefore prone to crystallization. Therefore homogeneous molecular dispersion is the primary factor for excellent stability even at high drug loading.

Example 16. Film Coated Tablet, Containing Spray Dried Solid Dispersion of Compound a with Copovidone (Poly(Vinylpyrrolidone-Co-Vinyl Acetate)(6+4))

The tablet contains 800 mg of the spray dried powder (SDP) of compound A and COPOVIDONE (Poly(vinylpyrrolidone-co-vinyl acetate) (6+4)), equivalent to 400 mg of compound A (free base).

TABLE 6

Tablet composition:

| Component[1] | Quantity (mg/tablet) | Function |
|---|---|---|
| Kernel | | |
| Compound A | 400.00 | Active ingredient |
| COPOVIDONE (Poly(vinylpyrrolidone-co-vinyl acetate) (6 + 4)) | 400.00 | Polymer |
| (compound A + COPOVIDONE (Poly(vinylpyrrolidone-co-vinyl acetate) (6 + 4))[2]) | (800.00) | Galenical intermediate |
| Mannitol (spray dried, 200)[3] | 68.00 | Filler |
| Croscarmellose sodium | 70.00 | Disintegrant |
| Crospovidone | 40.00 | Disintegrant |
| Colloidal silicon dioxide | 15.00 | Glidant |
| Magnesium stearate | 7.00 | Lubricant |
| Total kernel weight | 1000.00 | |
| Film Coat[4,5] | | |
| Polyvinyl alcohol, part. Hydrolyzed | 12.000 | Coating agent |
| Titanium dioxide | 6.234 | Color |
| Polyethylene glycol | 6.060 | Plasticizer |
| Talc | 4.440 | Glidant |
| Iron oxide yellow | 0.990 | Color |
| Iron oxide red | 0.240 | Color |
| Iron oxide black | 0.036 | Color |
| Total film coat weight | 30.000 | |
| Total film-coated tablet weight | 1030.00 | |

[1]Acetone is used in the spray drying process; it is essentially removed during processing,
[2]Spray Dried Powder (SDP) consisting of 50% compound A and 50% COPOVIDONE (Poly(vinylpyrrolidone-co-vinyl acetate) (6 + 4)).
[3]Can be used for compensation of the SDP potency
[4]Purified water (USP/Ph. Eur.) is used in aqueous film coating process; it is essentially removed during processing.
[5]A commercially available film coat mixture, e.g., Opadry II brown 85F26792, may be used.

Method Steps:
1) Dissolve compound A (50% w/w of the spray dried powder) and COPOVIDONE (Poly(vinylpyrrolidone-co-vinyl) (6+4)) (50% w/w of the spray dried powder) in Acetone to obtain a solid concentration of 5% (w/w).
2) The solution obtained in 1) if fed through a 4 filter to the spray-dryer unit and is atomized using a rotary wheel atomizer, or a two-fluid nozzle, or pressure nozzle in the drying chamber. The fine mist created by the atomizer mixes with the hot nitrogen stream (110 to 150) and evaporation of the solvents from the droplets begins. The feed rate of the solution is adjusted to achieve the desired gas outlet temperature (60 to 90). The drying gas carries the fine powder through the drying chamber out to the cyclone. The cyclone separates the powder from the drying gas and the powder is collected by gravity into drums. The substantially powder-free gas flows into a filter bag housing where very fine particles are retained in the bag filters. The powder free gas is cooled down in a condenser where solvent condensation occurs and the drying gas after re-heating is re-circulated to the drying to the drying chamber.
3) Perform secondary drying of the spray dried material obtained under 2) in order to reduce the amount of acetone present in the product. For secondary drying a tray dryer was used.
4) The spray dried powder as obtained under 3) was further blended with mannitol as a filler; Croscarmellose Sodium and Croscarmellose Sodium as disintegrants; colloidal silicon dioxide as glidant, using a tumble mixer.
5) The mixture obtained under 4) was further blended with magnesium stearate (0.2% of kernel weight) as lubricant in a tumble mixer.
6) The mixture obtained under 5) was dry granulated using a Gerteis Roller compactor equipped with either a pocket granulator or a star rotor and a screen with an opening of 0.8 mm.
Alternatively to the pocket granulator, a star rotor can be used. The opening can be between 0.5 mm and 0.8 mm.
7) The granules obtained under 6) were blended with colloidal silicon dioxide as glidant and croscarmellose sodium as disintegrant in a tumble mixer.
8) The blend obtained under 7) was further blended with magnesium stearate (0.5% of kernel weight) as lubricant in a tumble mixer in order to obtain the final blend for tablet compression.
9) The final blend was compressed to tablets using a rotary tableting maschine, e.g. Korsch XL 100 WipCon. The tablet weight was adjusted to the final dose strengths needed, i.e. 400 mg. These 400 mg kernels have a size of 20.1 mm to 9.5 mm
10) Tablets obtained under 9) are film coated using a perforated drum coater, e.g. Glatt Coater using a film coating system containing PVA. The amount of film coating applied is 3% of the kernel weight. The film coating consists of 1.2% Polyvinyl alcohol, part. Hydrolyzed, 0.6234% Titanium dioxide, 0.606% Polyethylene glycol, 0.444% Talc, 0.099% Iron oxide yellow, 0.024% Iron oxide red and 0.0036% Iron oxide black. The amount of film coating can be up to 5% of the kernel weight. Alternative film coating systems e.g. for moisture protection can also be used.

Example 17: Stability Data (XRPD Patterns) for the Solid Dispersion of Example 16 Upon Storage X-ray diffraction patterns were recorded at ambient conditions in transmission geometry with a STOE STADI P diffractometer (Cu K alpha radiation, primary monochromator, silicon strip detector, angular range 3° to 42° 2Theta, approximately 30 minutes total measurement time). The samples were prepared and analyzed without further processing (e.g. grinding or sieving) of the substance (FIGS. 8a, b)

Figure 8A:
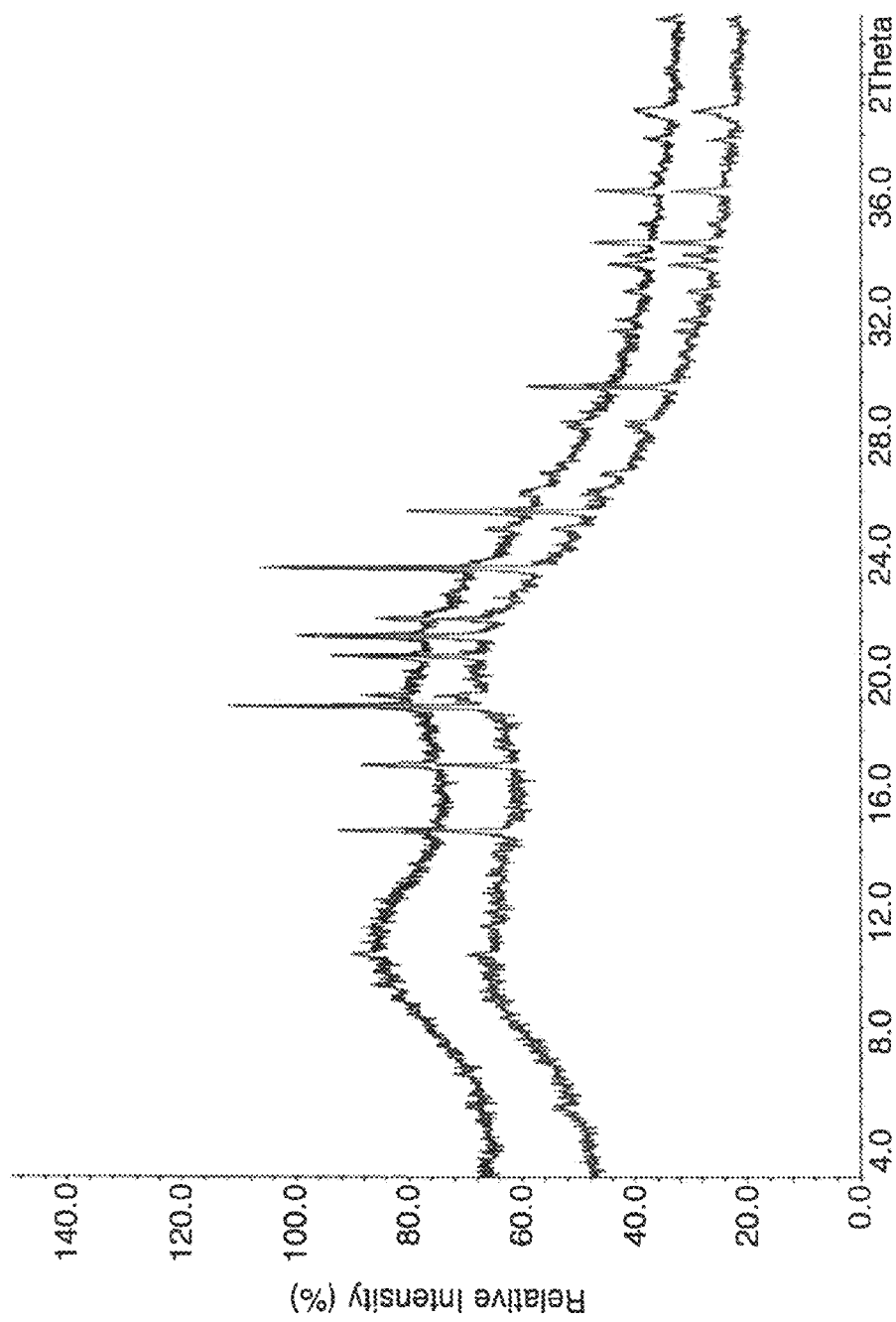
FIG. 8a illustrates the XRPD pattern of a Tablet obtained according to Example 16 (i.e. comprising spray dried solid dispersion of Compound A (50% wt/wt) with COPOVIDONE (Poly(vinylpyrrolidone-co-vinyl acetate) (6+4)) compared to placebo (Tablet without solid dispersion). The XRPD pattern of the Tablet corresponds to the pattern of the placebo, indicating that no crystalline API (Compound A) is detectable.

The XRPD pattern of the solid dispersion according to Example 16, i.e. spray dried solid dispersion comprising 50% of Compound A and COPOVIDONE (Poly(vinylpyrrolidone-co-vinyl acetate) (6+4)), corresponds to the pattern of the placebo, demonstrating that initially no crystalline API (Compound A) is detectable (FIG. 8a).

Figure 8B:
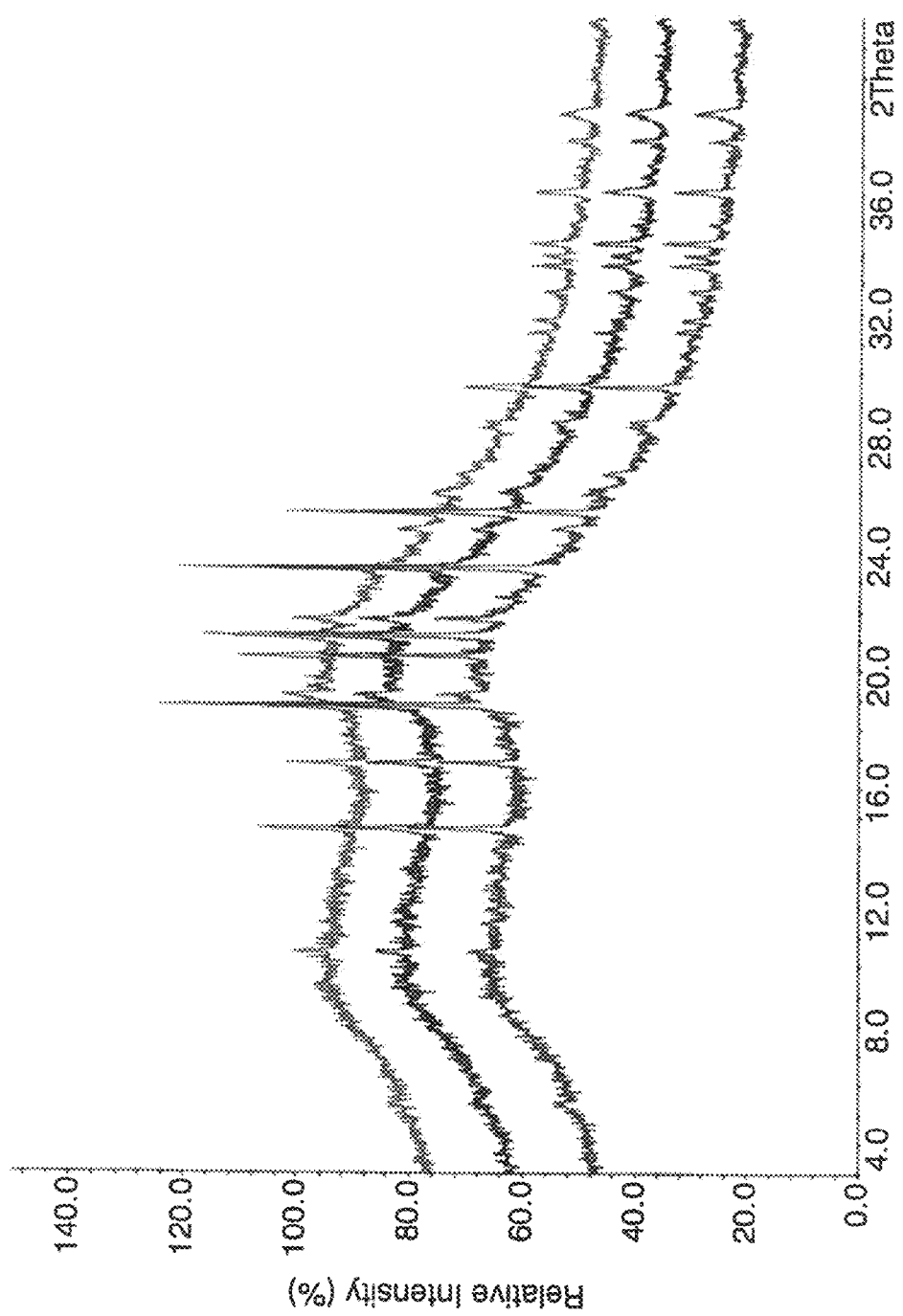
FIG. 8b illustrates the stability of the Tablet according to Example 16 over time, using X-ray powder diffraction. Comparison of the initial measurement for the Tablet (bottom curve) with the curves obtained after 3 months storage in duplex blisters (middle) and HDPE bottles (top) at 40° C. and 75 relative humidity (RH) indicates that no crystalline Compound A could be detected upon storage.

The XRPD patterns of said solid dispersion after 3 months of storage in duplex blisters and HDPE bottles (storage conditions: 40° C. and 75% relative humidity (RH)) correspond to the pattern of the initially measured solid dispersion, demonstrating that no crystalline API (Compound A) is detectable (FIG. 8b).

Example 18: Plasma Concentrations of Compound A Released from Different Formulations (In Vivo)

To assess the in vivo relative bioavailability (rBA) for Compound A from different pharmaceutical preparations, a clinical study (protocol NP28902 Part 2) is designed as a multiple-center, open-label, 3 period, 6 sequence, randomized crossover study in patients with solid tumors. Three different tablet formulations comprising Compound A are tested. These were:
a) the film coated tablet according to Example 8;
b) the film coated tablet according to Example 10; and
c) the film coated tablet according to Example 16.

Approximately 12 male and female patients older than 18 years of age from approximately 4-6 sites in the US and Canada receive, under fasting condition, 3 single-dose treatments (in random sequence or period) of Compound A p.o. 800 mg administered at least 7 days apart (in the morning of Day 1, Day 8, and Day 15). Blood samples for measurement of plasma concentrations of Compound A are collected periodically up to 7 days (or 168 hrs) post-dose and they are measured by LC MS/MS method. Pharmacokinetic (PK) parameters are derived from plasma concentrations via non compartmental methods. Primary PK parameters are $C_{max}$ and $AUC_{0-4}$ ($AUC_{last}$, if measurable 7 days post-dose) of Compound A and secondary PK parameters are $AUC_{last}$ or $AUC_{0-168\ h}$, $t_{max}$, $t_{1/2}$, and of Compound A.

Figure 9:
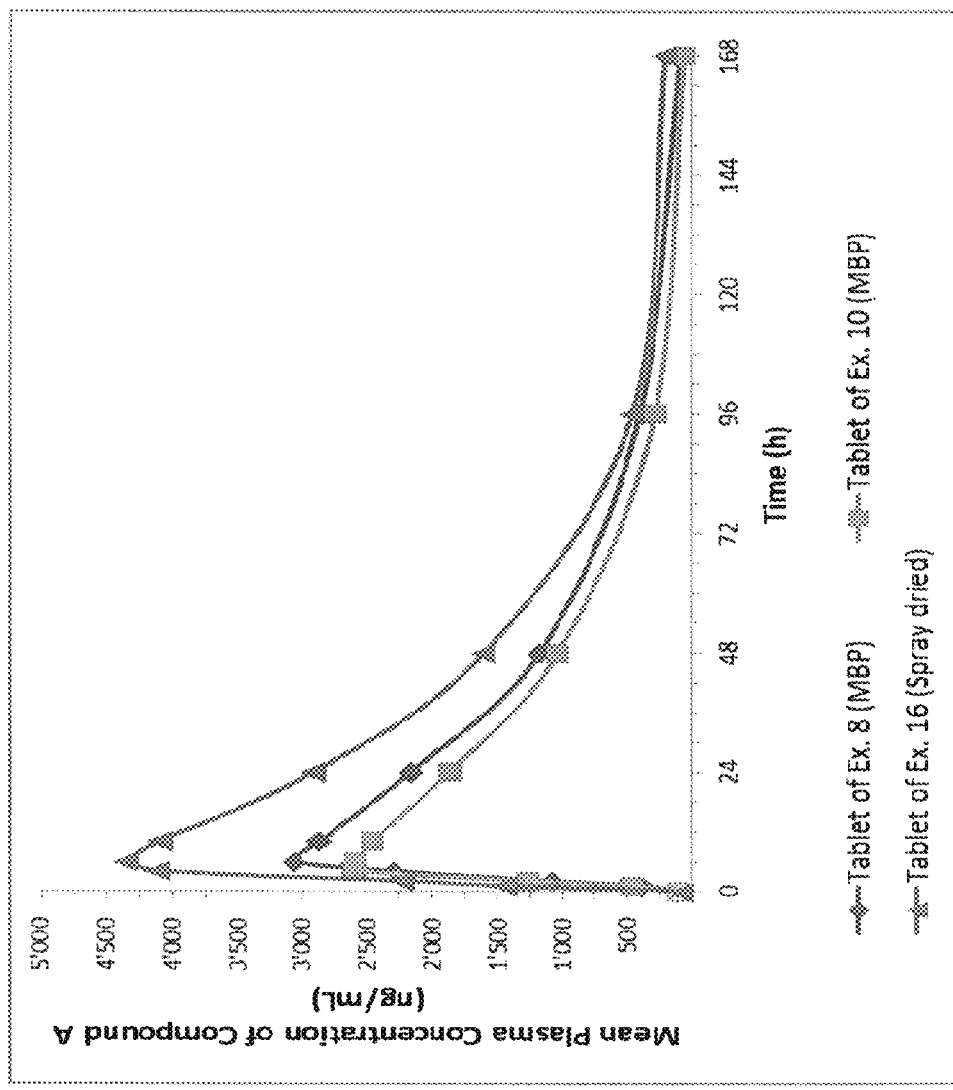
FIG. 9 illustrates comparative in vivo plasma concentration data for Compound A released from 3 different tablet formulations, i.e. tablets according to Examples 8, 10 and 16.

The mean plasma concentrations of Compound A release from the tested formulations is provided in FIG. 9.

Media Composition 0.01 N HCl (1 L)

Weigh (0.83 ml) HCL37% fuming in a 1000 ml volumetric flask prefilled with 500 ml of dest. water and fill up to 1000 ml. Mix well, allow to cooling to room temperature before use.

FaSSIF (3 L)

Step 1

To prepare buffer, dissolve 1.260 g of NaOH (pellets), 13.410 g of $NaH_2PO_4$ Dihydrate and 18.558 g of NaCl, in about 2.700 L of purified water. Adjust the pH to 6.5 with either 1 N NaOH or 1 N HCl. Make up to volume (3.000 L) with purified water at room temperature.

Step 2

Add 6.720 g of SIF Powder Original to about 1.5 L of buffer. Stir until powder is completely dissolved. Make up to volume (3.000 L) with buffer at room temperature.

The dissolution data obtained according to this method are disclosed in FIG. 9.

The invention claimed is:

1. A physically stable solid dispersion, comprising a compound having an aqueous solubility of less than 1 µg/ml and a melting point of >270° C. together with a stabilizing polymer, wherein the compound having an aqueous solubility of less than 1 µg/ml is 4-{[(2R, 3S, 4R, 5S)-4-(4-Chloro-2-Fluoro-Phenyl)-3-(3-Chloro-2-Fluoro-Phenyl)-4-Cyano-5-(2,2-Dimethyl-Propyl)-Pyrrolidine-2-Carbonyl]-Amino}-3-Methoxy-Benzoic Acid (Compound A):

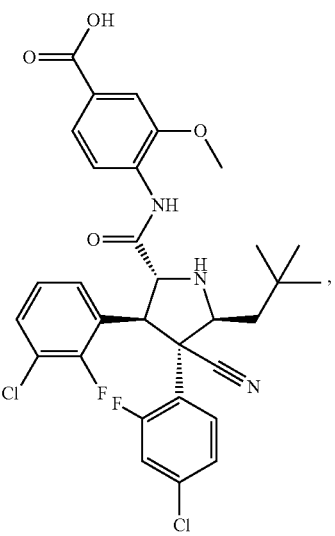 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

and wherein the stabilizing polymer is EUDRAGIT® L-100 (Poly(methacrylic acid)-co-methyl methacrylate) or Eudragit® L100-55 (Poly(methacrylic acid)-co-methyl methacrylate).

2. The solid dispersion according to claim 1 wherein the ratio of the amount by weight of Compound A within the solid dispersion to the amount by weight of the stabilizing polymer therein is between 5:95 to 70:30.

3. The solid dispersion of claim 1 wherein the ratio of the amount by weight of the Compound A within the solid dispersion to the amount by weight of the stabilizing polymer therein is 30:70 to 50:50.

4. A unit dose solid formulation comprising: the solid dispersion according to claim 1, together with commonly used pharmaceutical ingredients selected from the group consisting of disintegrants, diluents, lubricants and glidants together with a film coat.

5. A method for preparing a solid dispersion according to claim 1, comprising the steps of forming a solution of Compound A and the polymer in dimethyl-acetamide, or any other suitable solvent and co-precipitating Compound A with the polymer using anti-solvent.

6. A pharmaceutical preparation containing the solid dispersion according to claim 1, together with additional pharmaceutically acceptable adjuvants.

7. A method of treating prostate cancer, comprising the step of administering a therapeutically effective amount of the physically stable solid dispersion according to claim 1 to a patient in need thereof.

* * * * *

UNITED STATES PATENT AND TRADEMARK OFFICE
CERTIFICATE OF CORRECTION

PATENT NO. : 10,034,854 B2
APPLICATION NO. : 15/200419
DATED : July 31, 2018
INVENTOR(S) : Steve Lomuscio et al.

Page 1 of 1

It is certified that error appears in the above-identified patent and that said Letters Patent is hereby corrected as shown below:

On the Title Page

Item (73) Assignee name should read as follows:
--Hoffmann-La Roche Inc., Nutley, NJ (US)--

Signed and Sealed this
Second Day of October, 2018

Andrei Iancu
*Director of the United States Patent and Trademark Office*